US007879979B2

(12) United States Patent  
Buechler et al.

(10) Patent No.: US 7,879,979 B2
(45) Date of Patent: Feb. 1, 2011

(54) ARGININE ANALOGS, AND METHODS FOR THEIR SYNTHESIS AND USE

(75) Inventors: Kenneth F. Buechler, Rancho Santa Fe, CA (US); Mariusz G. Banaszczyk, San Marcos, CA (US); Joseph Barry Noar, Solana Beach, CA (US); Violeta Dinauer, San Diego, CA (US)

(73) Assignee: Alere International, Waltham, MA (US)

( * ) Notice: Subject to any disclaimer, the term of this patent is extended or adjusted under 35 U.S.C. 154(b) by 474 days.

(21) Appl. No.: 11/795,173

(22) PCT Filed: Jan. 19, 2006

(86) PCT No.: PCT/US2006/001892

§ 371 (c)(1),
(2), (4) Date: Aug. 8, 2008

(87) PCT Pub. No.: WO2006/078813

PCT Pub. Date: Jul. 27, 2006

(65) Prior Publication Data

US 2008/0293920 A1 Nov. 27, 2008

Related U.S. Application Data

(60) Provisional application No. 60/646,221, filed on Jan. 21, 2005.

(51) Int. Cl.
*C07K 16/00* (2006.01)
*C07D 333/32* (2006.01)
(52) U.S. Cl. .................... 530/363; 549/62; 562/561
(58) Field of Classification Search ............... 530/363; 549/62; 562/561
See application file for complete search history.

(56) References Cited

U.S. PATENT DOCUMENTS

| | | | |
|---|---|---|---|
| 5,480,792 A | 1/1996 | Buechler et al. |
| 5,525,524 A | 6/1996 | Buechler et al. |
| 5,631,171 A | 5/1997 | Sandstrom et al. |
| 5,643,575 A | 7/1997 | Martinez et al. |
| 5,672,662 A | 9/1997 | Harris et al. |
| 5,679,526 A | 10/1997 | Buechler et al. |
| 5,705,153 A | 1/1998 | Shorr et al. |
| 5,730,990 A | 3/1998 | Greenwald et al. |
| 5,763,189 A | 6/1998 | Buechler et al. |
| 5,824,799 A | 10/1998 | Buechler et al. |
| 5,851,776 A | 12/1998 | Valkirs |
| 5,885,527 A | 3/1999 | Buechler |
| 5,902,588 A | 5/1999 | Greenwald et al. |
| 5,922,615 A | 7/1999 | Nowakowski et al. |
| 5,932,462 A | 8/1999 | Harris et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,113,855 A | 9/2000 | Buechler |
| 6,143,576 A | 11/2000 | Buechler |
| 6,238,931 B1 | 5/2001 | Buechler et al. |
| 6,251,687 B1 | 6/2001 | Buechler et al. |
| 6,747,273 B2 * | 6/2004 | Brame et al. ........... 250/283 |

FOREIGN PATENT DOCUMENTS

| | | |
|---|---|---|
| DE | 10111049 A1 | 9/2002 |
| WO | WO 95/08772 | 3/1995 |
| WO | WO 2004/046314 | 6/2004 |

OTHER PUBLICATIONS

Antibodies: A Laboratory Manual, E.Harlow and D.Lane eds., Cold Spring Harbor Laboratory, p. 78-87, (Cold Spring Harbor, NY, 1988).
Antibodies: A Laboratory Manual, E.Harlow and D.Lane eds., Cold Spring Harbor Laboratory, p. 55-120N, (Cold Spring Harbor, NY, 1988).
Gibson et al., Nonpetidic $\alpha_\nu\beta_3$ Integrin Antagonist Libraries: On-Bead Screening and Mass Spectrometric Identification without Tagging,Agnew. Chem. Int. Ed. 40: 165, (2001).
Gottschling et al., Cellular solid-Phase Binding Assay and Mass Spectrometry for Screening of $\alpha 4\beta 7$ Integrin Antagonists, Bioorg. Med. Chem. Lett 11: 2997, (2001).
Leon et al., Evaluation of Resins for On-Bead Screening: A Study of Papain and Chymotrypsin Specificity Using Pega-Bound Combinatorial Peptide Libraries, Bioorg. Med. Chem. Lett. 8:2997-3002, (1998).
Ng, Jocelyn H. and liag, Leodevico L., Biomedical applications of protein chips, J.Cell Mol. Med., 6:329-340, (2002).
Orain, David and Bradley, Mark, Solid phase synthesis of trypanothione reductase inhibitors—towards single bead screening, Tetrahedron Lett. 42: 515, (2001).
Papanikos et al., α-Ketocarbonyl Peptides: A General Approach to Reactive Resin-Bound Intermediates in the Synthesis of Peptide Isosteres for Protease Inhibitor Screening on Solid Support, J. Am. Chem. Soc. 123:2176-2181, (2001).
Smith, Helen K., and Bradley, Mark , Comparison of Resin and Solution Screening Methodologies in Combinatorial Chemistry and the Identification of a 100 nM Inhibitor of Trypanothione Reductase, J. Comb. Chem. 1:326-332, (1999).
Topchieva et al., Synthesis and Physicochemical Properties of Protein Conjugates with Water-soluble Poly(alkylene oxides), Bioconjugate Chem. 6:380-388, (1995).

(Continued)

*Primary Examiner*—Rei-tsang Shiao
(74) *Attorney, Agent, or Firm*—Wilson Sonsini Goodrich & Rosati

(57) ABSTRACT

The present invention relates to novel arginine analogs, and methods for their synthesis and use. Such analogs are designed to provide a protected or free thiol (—SH) group, thereby providing a convenient linkage chemistry for coupling to a suitable group on a target such as a protein, polypeptide, detectable label or solid phase, and at a site distal to the guanidino group. Arginine analog conjugates are useful for generating antibodies that can bind specifically with dimethylarginine, which can be detected using such antibodies in immunoassays.

25 Claims, No Drawings

OTHER PUBLICATIONS

Wilson et al., Simplified conjugation chemistry for coupling peptides to F(ab') fragments: autologous red cell agglutination assay for HIB-1 antibodies, *J. Immunol. Methods* 175:267-273, (1994).

Yarmush et al., Coupling of antibody-binding fragments to solid-phase supports: site-directed binding of F(ab')$_2$ fragments, *J. Biochem. Biophys. Methods* 25:285-297, (1992).

International search report dated Sep. 26, 2006 for PCT Application No. US06/01892.

* cited by examiner

US 7,879,979 B2

ARGININE ANALOGS, AND METHODS FOR THEIR SYNTHESIS AND USE

FIELD OF THE INVENTION

The present invention relates to novel arginine analogs useful for preparing conjugates comprising, inter alia, proteins, polypeptides, and labels; to conjugates comprising such arginine analogs, and to methods for their synthesis and use.

BACKGROUND OF THE INVENTION

The following discussion of the background of the invention is merely provided to aid the reader in understanding the invention and is not admitted to describe or constitute prior art to the present invention.

Asymmetric dimethylarginine (ADMA) is an arginine derivative formed by methylation of arginine residues in proteins, followed by protein hydrolysis. ADMA has been reported to regulate rates of nitric oxide (NO) formation, which can act as a signal molecule in the nervous system, an anti-infective, a regulator of blood pressure, and a regulator of blood flow. Elevated ADMA is reportedly a risk factor for hypertension, cardiovascular disease, renal failure, and erectile dysfunction. Factors contributing to elevated ADMA include increased oxidative challenge and folic acid insufficiency. See, e.g., WO04046314, which is hereby incorporated in its entirety.

In developing a binding assay for ADMA, the artisan must consider that samples may contain symmetrical dimethylarginine (SDMA) and/or arginine. Thus, immunogenic and label conjugates should be designed to present arginine or its N-methyl derivatives in a manner that permits specific recognition and discrimination of molecules which differ only in the methylation state of the two equivalent nitrogens on the guanidino group. Analogs for use in preparing such conjugates should also be designed to provide convenient attachment to various proteins, polypeptides, and labels under mild conditions.

BRIEF SUMMARY OF THE INVENTION

It is an object of the invention to provide novel arginine analogs, and methods for their synthesis and use. Such analogs are designed to provide a free thiol (—SH) group, providing a linkage chemistry for convenient coupling to a suitable group on a target protein, polypeptide, or label, and at a site distal to the guanidino group.

In a first aspect then, the invention relates to compounds (or salts thereof) having the following general formula:

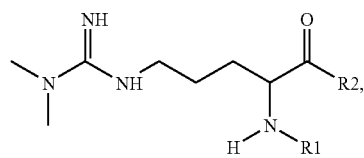

where one or both of $R^1$ and $R^2$ provide a terminal thiol or protected thiol. Most preferably, one but not both of $R^1$ or $R^2$ is such a linking group.

In certain preferred embodiments, $R^1$ is —H or a conjugating group having the structure:

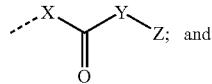

$R^2$ is —OH or a conjugatiing group having the structure:

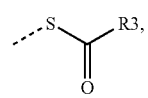

X is $C_{1-4}$ unsubstituted alkylene, and is optionally present;

Y is an optionally substituted $C_{1-4}$ alkylene or N(H)—$C_{1-6}$ alkylene, and is optionally present; and Z is a moiety providing a thiol or a protected thiol at its terminus.

The choice of Z may be varied by the artisan, depending on the desired length and composition for a crossbridge to a protein, polypeptide or label, and whether the Z thiol is in free (—SH) or in protected form. In the latter case, a wide variety of thiol protective groups are known in the art. See, e.g., standard reference works such as Greene and Wuts, PROTECTIVE GROUPS IN ORGANIC SYNTHESIS, 3$^{rd}$ edition, John Wiley & Sons Inc., 1999, which is hereby incorporated by reference in its entirety. As described therein, and as recognized in the art, suitable thiol protective groups include thioesters, thioethers, unsymmetrical disulfides, and sulfenyls.

In preferred embodiments, Z is a 5- or 6-member cyclic thiolactone, an optionally substituted $C_{1-4}$ thiol-substituted alkyl, or an optionally substituted thioester having the structure:

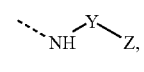

where $R^3$ is selected from the group consisting of optionally substituted $C_{1-4}$ alkyl, optionally substituted $C_{1-4}$ alkoxy, and optionally substituted aryl.

In each of the embodiments described herein, substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$.

In those embodiments where $R^2$ is a conjugating group having the structure:

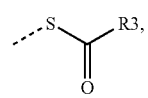

and Z provides a protected thiol, Z is preferably a thiolactone, most preferably having 5 ring atom members. In such embodiments, Y is preferably not present. Alternatively, Z is a thioester. In these embodiments, Y is preferably optionally substituted N(H)—C$_{0-6}$ alkylene. A particularly preferred Y has the structure —N(H)CH$_2$C(O)CH$_2$—.

In certain of these particularly preferred embodiments, R$^3$ is selected from the group consisting of —CH$_3$, —CH$_2$CH$_3$, —OCH$_3$, —OCH$_2$CH$_3$, —OCH$_2$C$_6$H$_5$, —OCH$_2$CH$_2$C$_6$H$_5$, and —C$_6$H$_5$.

In those embodiments where R$^2$ is a conjugating group providing an unprotected thiol, R$^2$ preferably has the structure:

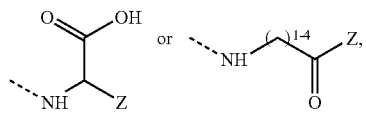

where Z is preferably an alkyl thiol such as —CH$_2$SH, —CH$_2$CH$_2$SH, or —CH(COOH)CH$_2$CH$_2$SH.

In those embodiments where R$^1$ is a conjugating group having the structure:

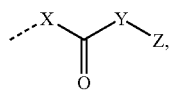

and Z provides a protected thiol, Z is preferably a thiolactone, most preferably having 5 ring atom members. In such embodiments, X is most preferably C$_{0-4}$ unsubstituted alkylene, and Y is most preferably N(H). Alternatively, Z is a thioester. In these embodiments, Y is most preferably C$_{0-4}$ alkylene and X is most preferably absent. Again, a particularly preferred Y has the structure:

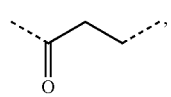

and in certain of these particularly preferred embodiments, R$^3$ is selected from the group consisting of —CH$_3$, —CH$_2$CH$_3$, —OCH$_3$, —OCH$_2$CH$_3$, —OCH$_2$C$_6$H$_5$, —OCH$_2$CH$_2$C$_6$H$_5$, and —C$_6$H$_5$.

In those embodiments where R$^1$ is a conjugating group providing an unprotected thiol, X is most preferably C$_{0-4}$ unsubstituted alkylene, Y is most preferably absent or N(H), and Z is most preferably a C$_{1-4}$ thiol-substituted alkyl. In particularly preferred embodiments, Z preferably has the structure:

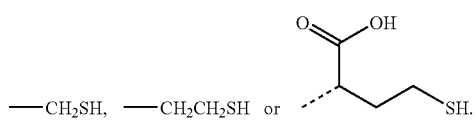

Most preferred compounds from the various embodiments described above may be one or more of the following:

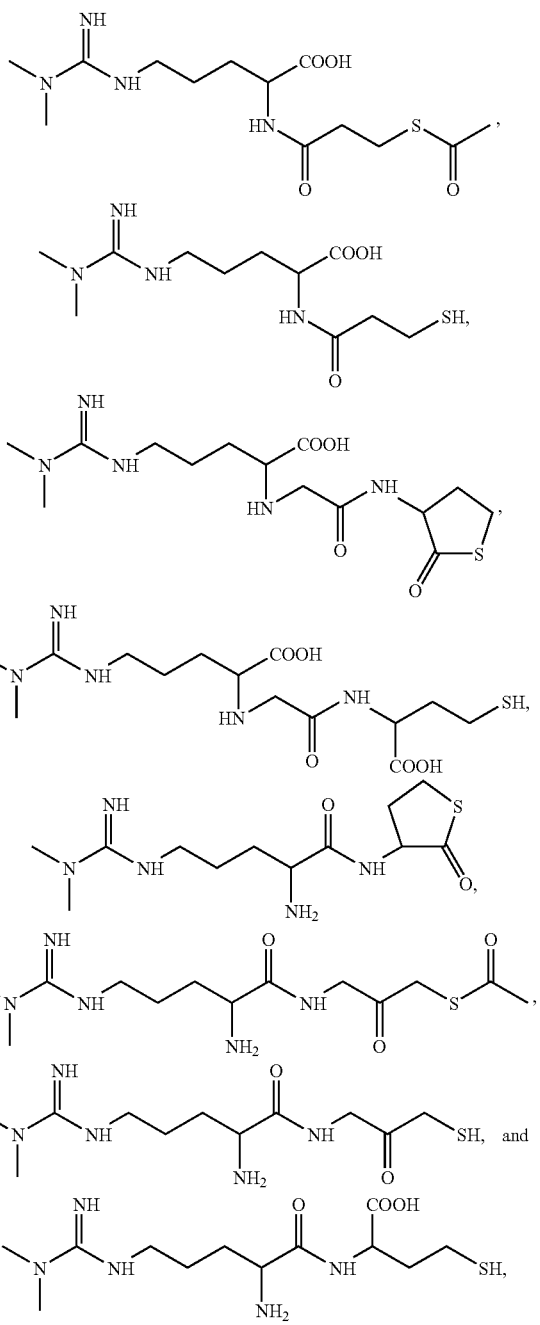

or salts thereof.

In a related aspect, the invention relates to compositions comprising one or more of the foregoing compounds (or their salts) covalently linked through the terminal thiol provided by R$^1$ and/or R$^2$ to a protein, polypeptide, label, or other molecule, to form what is referred to herein as "arginine analog conjugates."

In the case of compounds of the invention comprising an unprotected thiol, the compounds may be directly linked to an appropriate target protein, polypeptide, label, or other molecule to form a conjugate via any thiol-directed coupling group on the target molecule. Exemplary thiol-directed coupling groups are described hereinafter, and methods for incorporating such coupling groups into target molecules for conjugation to the compounds described above are well known in the art. In the case of compounds of the invention comprising a protected thiol, removal of the protective group provides a free thiol, which is then linked to any thiol-directed coupling group on the target molecule in a similar fashion.

Preferred coupling groups on target molecules are maleimides, which can readily be linked according to the following reaction scheme:

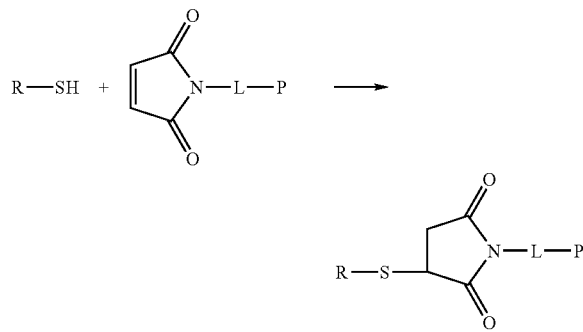

where R—SH is a compound of the invention comprising a free thiol (either as a free thiol or following deprotection of a protected thiol), L is a linkage chemistry, and P is a target protein, polypeptide, label, or other molecule. L is preferably a covalent bond, or a linker comprising 1-10 backbone atoms, of which 0-4 backbone (i.e., non-substituent) atoms are heteroatoms, wherein L is optionally substituted with from 1 to 4 substituents independently selected from the group consisting of $C_{1-6}$ alkyl straight or branched chain, —$NO_2$, —$NH_2$, =O, halogen, trihalomethyl, $C_{1-6}$ alkoxy, —OH, —$CH_2OH$, and —$C(O)NH_2$.

Thus, maleimide-based conjugates according to the invention are typically characterized by one of the following structures:

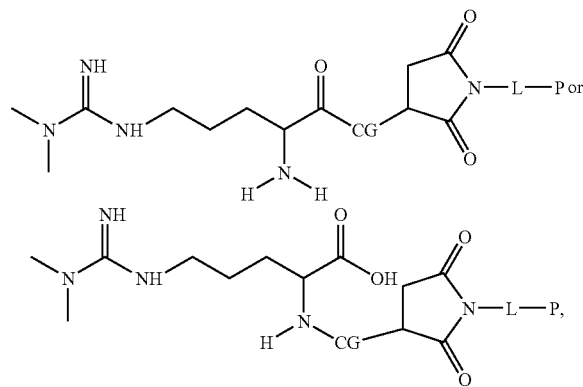

wherein:

CG is a conjugating group, covalently bound to the maleimide moiety through a thiol linkage derived from $R^1$ or $R^2$, and L and P are as defined above.

In certain embodiments, P is a protein, most preferably an immunogenic protein which can be used to raise an immune response to an epitope that includes a compound of the invention using a so-called "hapten-carrier" immunogen. Common carrier proteins include bovine serum albumin, keyhole limpet hemocyanin, ovalbumin, etc. Protocols for conjugation of haptens to carrier proteins may be found in ANTIBODIES: A LABORATORY MANUAL, E. Harlow and D. Lane, eds., Cold Spring Harbor Laboratory (Cold Spring Harbor, N.Y., 1988) pp. 78-87, which is hereby incorporated by reference.

Alternatively, P may preferably be a detectable label. Preferred detectable labels may include molecules or larger structures that are themselves detectable (e.g., fluorescent moieties, electrochemical labels, metal chelates, latex particles, etc.), as well as molecules that may be indirectly detected by production of a detectable reaction product (e.g., enzymes such as horseradish peroxidase, alkaline phosphatase, etc.) or by a specific binding molecule which itself may be detectable (e.g., biotin, avidin, streptavidin, digoxigenin, maltose, oligohistidine, 2,4-dintrobenzene, phenylarsenate, ssDNA, dsDNA, etc.). Exemplary conjugation to such detectable labels is described hereinafter. Particularly preferred detectable labels are fluoresent latex particles.

The foregoing lists of suitable target molecules are not meant to be limiting. Further exemplary embodiments are described hereinafter. In addition, numerous other classes of suitable targets, including peptide hormones, therapeutic proteins, antibodies, antibody fragments, single-chain variable region fragments, small molecules, nucleic acids, oligosaccharides, polysaccharides, cyclic polypeptides, peptidomimetics, aptamers and solid phases are known in the art.

While a conjugation target may be conjugated 1:1 with an arginine analog of the invention, an individual target may also comprise more than 1 conjugation site, and hence more than 1 compound of the invention conjugated thereto. In preferred embodiments, a conjugation target comprises at least 10 arginine analog moieties covalently bound thereto, more preferably at least 30, still more preferably at least 50, and most preferably at least 100.

In still other related aspects, the present invention relates to methods for the production and use of the arginine analog conjugates of the present invention.

Such methods can comprise contacting one or more compounds of the invention comprising a free thiol with one or more target molecules comprising one or more thiol-directed coupling groups, under conditions where the free thiol(s) react with the thiol-directed coupling group(s) to form one or more conjugates. Conditions for such reactions are dependent upon the thiol-directed coupling group(s) selected, and are well known to the skilled artisan. Exemplary conditions are described hereinafter.

Such methods may further comprise the step of deprotecting a protected thiol from one or more compounds of the invention prior to said contacting step, and/or attaching one or more thiol-directed coupling groups to a protein, polypeptide, label, or other molecule to form an appropriate conjugation target. In the latter case, this may comprise the use of bifunctional cross-linkers that provide an appropriate thiol-directed coupling group at one site in the molecule, and a second coupling group for attachment to the protein, polypeptide, label, or other molecule of interest. Numerous bifunctional cross-linkers are well known to those of skill in the art.

Regarding the use of such arginine analog conjugates, the present invention related to methods for preparing an antibody. These methods comprise using one or more conjugates as an immunogen to stimulate an immune response. Such methods may comprise administering one or more conjugates of the invention in accordance with a suitable immunization protocol, and separating an appropriate antibody from a body fluid of the animal. Exemplary protocols for preparing immunogens, immunization of animals, and collection of antiserum may be found in ANTIBODIES: A LABORATORY MANUAL, E. Harlow and D. Lane, eds., Cold Spring Harbor Laboratory (Cold Spring Harbor, N.Y., 1988) pp. 55-120, which is hereby incorporated by reference. Alternatively, the arginine analog conjugates of the present invention may be used in phage display methods to select phage displaying on their surface an appropriate antibody, followed by separation of nucleic acid sequences encoding at least a variable domain region of an appropriate antibody. Phage display methods are well known to those of skill in the art. Such methods may use immunized or unimmunized animals as a source of nucleic acids to form the phage display library. Antibodies prepared in this manner may preferably find use as therapeutic molecules and/or as receptors in receptor binding assays. Preferably, such antibodies bind asymmetric dimethylarginine with an affinity that is at least a factor of 5, more preferably at least a factor of 10, still more preferably at least a factor of 30, and most preferably at least a factor of 50 or more, than an affinity for symmetric dimethylarginine and/or arginine.

Other uses of the arginine analog conjugates may comprise the use of such a conjugate to prepare detectable labels, preferably for use in a receptor binding assay. Examples of such assays include immunoassays, preferably a competitive binding assay for asymmetric dimethylarginine. Examples of such assays are described hereinafter. Preferably, such assays provide a signal for asymmetric dimethylarginine that is at least a factor of 5, more preferably at least a factor of 10, still more preferably at least a factor of 30, and most preferably at least a factor of 50 or more, than a signal obtained from an equimolar amount of symmetric dimethylarginine and/or from an equimolar amount of arginine.

These assay methods can utilize arginine analog-labels in various homogenous, sandwich, competitive, or non-competitive assay formats, to generate a signal that is related to the presence or amount of an arginine analog (e.g., asymmetric dimethylarginine) of interest in a test sample. Certain preferred assays are competitive immunoassays. In these immunoassay methods, a test sample is contacted with one or more arginine analogs conjugated to a solid phase according to the methods described herein, and with an antibody conjugated to a signal development element, whereby arginine analog(s) of interest present in the sample compete with the arginine analog(s) conjugated to a solid phase for binding to the labeled antibody. Alternatively, a test sample is contacted with one or more arginine analogs conjugated to a signal development element according to the methods described herein, and with an antibody conjugated to a solid phase, whereby arginine analog(s) of interest present in the sample compete with the arginine analog(s) conjugated to a signal development element for binding to the labeled antibody. In either case, the signal obtained is inversely related to the amount of the arginine analog(s) of interest present in the sample.

Other embodiments of the invention will be apparent from the following detailed description, exemplary embodiments, and claims.

DETAILED DESCRIPTION OF THE INVENTION

The present invention relates in part to amino acid analogs and methods and for their production and use, particularly for preparing cross-linkable thiol-containing arginine analogs for conjugation to another molecule. These analogues are advantageously designed to present an arginine side chain that is free of chemical modifications required for conjugation of the analog to a conjugation target such as a protein, polypeptide, detectable label, solid phase, etc. The analogs of the present invention are particularly well suited for producing antibodies and labels for use in receptor binding assays for ADMA that can distinguish ADMA from SDMA and arginine itself.

As described herein, the compounds (or salts thereof) of the present invention have the following general formula:

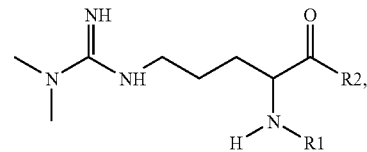

where one or both of $R^1$ and $R^2$ provide a terminal thiol or protected thiol. Most preferably, one but not both of $R^1$ or $R^2$ is such a linking group.

For the sake of clarity, definitions for the following terms regarding the compounds of the present invention are provided.

As used herein, the term "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. Preferably, the aryl is either optionally substituted phenyl, optionally substituted pyridyl, optionally substituted benzothiopyranyl, optionally substituted carbazole, optionally substituted naphthyl, optionally substituted tetrahydronaphthyl. While "aryl" is most preferably a monocyclic carbocyclic aromatic ring having 5 or 6 ring atoms (and is most preferably phenyl), the aryl or heteroaryl Ar group (formed into an arylene or heteroarylene in the crosslinkers described herein by elaboration from a ring atom) generally may contain up to ten ring atoms, although the skilled artisan will recognize that aryl groups with more than ten ring atoms are within the scope of the invention. The ring systems encompassed by Ar can contain up to four heteroatoms, independently selected from the group consisting of N, S, and O.

Monocyclic aryl groups include, but are not limited to: phenyl, thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Fused bicyclic Ar groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties.

As used herein, the term "heteroatom" as used herein refers to non-carbon, non-hydrogen atoms such as N, O, and S.

The aryl group may also be optionally substituted by replacement of one or more hydrogen atoms by another chemical moiety. Preferred substituents include $C_{1-6}$ alkyl straight or branched (e.g. isopropyl) chain, halogen, trihalomethyl, alkoxy, $NO_2$, $NH_2$, OH, —COOR', where R' is H or lower alkyl, $CH_2OH$, and $CONH_2$.

As used herein, the term "alkyl" refers to a monovalent saturated aliphatic hydrocarbon including straight chain and branched chain groups. Preferably, the alkyl group has 1 to 20 carbon atoms. More preferably, it is a medium alkyl (having 1 to 10 carbon atoms). Most preferably, it is a lower alkyl (having 1 to 4 carbon atoms). The alkyl group may be substituted or unsubstituted.

As used herein, the term "alkylene" refers to a divalent saturated aliphatic hydrocarbon including straight chain and branched chain groups. Preferably, the alkylene group has 1 to 20 carbon atoms. More preferably, it is a medium alkylene (having 1 to 10 carbon atoms). Most preferably, it is a lower alkylene (having 1 to 4 carbon atoms). The alkylene group may be substituted or unsubstituted.

As used herein, the term "alkoxy" group refers to both an —O-alkyl and an —O-cycloalkyl group; preferably an alkoxy group refers to a lower alkoxy, and most preferably methoxy or ethoxy.

As used herein, the term "thiolactone" refers to a cyclic hydrocarbon having 5 or 6 ring atoms, one of which is an S heteroatom, and where the heteroatom is adjacent to a carbon substituted with a =O.

As used herein, the term "thioester" refers to an organic compound having the structure R—S—C(O)—R'.

As used herein, the term "thiol-substituted alkyl" refers to an alkyl group containing an —SH group. Thiols are also referred to as "thio alcohols" and "sulfhydryls."

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

The term "polypeptide" as used herein refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and derivatives. The term protein refers to a polypeptide that is isolated from a natural source, or produced from an isolated cDNA using recombinant DNA technology, and that has a sequence of amino acids having a length of at least about 200 amino acids.

The term "nucleic acids" as used herein shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of purine or pyrimidine bases, or modified purine or pyrimidine bases.

The term "aptamer" as used herein is a single-stranded or double-stranded oligodeoxyribonucleotide, oligoribonucleotide or modified derivatives that specifically bind and alter the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The term "polysaccharide" as used herein refers to a molecule comprising more than 10 glycosidically linked monosaccharide residues, while the term "oligosaccharide" refers to a molecule comprising from 2-10 glycosidically linked monosaccharide residues.

The term "small molecule" includes any molecule having a molecular weight less than about 5,000 daltons (Da), preferably less than about 2,500 Da, more preferably less than 1,000 Da, most preferably less than about 500 Da.

Functional Moieties

Chemical cross-linkers are valuable tools for preparing antibody-detectable label conjugates, immunotoxins and other labeled protein and nucleic acid reagents. These reagents may be classified on the basis of the following:

1. Functional groups and chemical specificity;
2. length and composition of the cross-bridge;
3. whether the cross-linking groups are similar (homobifunctional) or different (heterobifunctional);
4. whether the groups react chemically or photochemically;
5. whether the reagent is cleavable; and
6. whether the reagent can be radiolabeled or tagged with another label.

As the compounds of the present invention provide an available thiol to act as an attachment point, targets may be prepared to provide an appropriate thiol-reactive site. Cross-linking reagents that couple through sulfhydryls (thiols) are available from many commercial sources. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Such reagents may be bifunctional, in that a second site on the reagent is available for use in modifying a conjugation target to incorporate the thiol-reactive site. In addition to thiols, reactive groups that can be targeted using a cross-linker include primary amines, carbonyls, carbohydrates and carboxylic acids. In addition, many reactive groups can be coupled nonselectively using a cross-linker such as photoreactive phenyl azides. Thus, a two-step strategy allows for the coupling of a protein that can tolerate the modification of its amines to an arginine analog of the invention. For suitable reagents, see Pierce 2003-2004 Applications Handbook and Catalog # 1600926, which is hereby incorporated by reference. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

Many factors must be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length cross-linkers and analyzing the success of conjugation. The use of cross-linkers with different reactive groups and/or spacer arms may be desirable when the conformation of the protein changes such that hindered amino acids become available for cross-linking.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, while intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380-8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety may be made empirically in order to best preserve a biological property of interest (e.g., binding affinity of an antibody, catalytic activity of an enzyme, etc.)

1. Coupling through Amine Groups

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.

2. Coupling through Sulfhydryl Groups

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

3. Coupling Through Carboxyl Groups

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

4. Nonselective Labeling

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

5. Carbonyl Specific Cross-Linkers

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

Exemplary Applications for Use of Cross-Linkable Arginine Analogs

1. Carrier Protein-Hapten/Peptide/Polypeptide Conjugates for Use as Immunogens

Numerous companies offer commercially available products in this area of immunological research. There are many cross-linkers used for the production of these conjugates, and the best choice is dependent on the reactive groups present on the hapten and the ability of the hapten-carrier conjugate to function successfully as an immunogen after its injection. Carbodiimides are good choices for producing peptide carrier conjugates because both proteins and peptides usually contain several carboxyls and primary amines. Other cross-linkers can also be used to make immunogen conjugates.

Adjuvants are mixtures of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Adjuvants have four main modes of action: enhanced antigen uptake and localization, extended antigen release, macrophage activation, and T and B cell stimulation. The most commonly used adjuvants fall into six categories: mineral salts, oil emulsions, microbacterial products, saponins, synthetic products and cytokines. A more extensive discussion of adjuvants and their use in immunization protocols is given in IMMUNOLOGY METHODS MANUAL, vol. 2, I. Lefkovits, ed., Academic Press, San Diego, Calif., 1997, ch. 13, which is hereby incorporated in its entirety.

Small molecules such as asymmetric dimethylarginine are not usually immunogenic, even when administered in the presence of adjuvant. In order to generate an immune response to these compounds, it is often necessary to attach them to a protein or other compound, termed a carrier, that is immunogenic. When attached to a carrier protein the small molecule immunogen is called a hapten. Haptens are also conjugated to carrier proteins for use immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore important to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Keyhole limpet hemocyanin (KLH) is a respiratory protein found in mollusks. Its large size makes it very immunogenic, and the large number of lysine residues available for conjugation make it very useful as a carrier for haptens such as asymmetric dimethylarginine. The phylogenic separation between mammals and mollusks increases the immunogenicity and reduces the risk of cross-reactivity between antibodies against the KLH carrier and naturally occurring proteins in mammalian samples.

2. Solid-Phase Immobilization

The arginine analogs and/or conjugates of the present invention can be immobilized on solid-phase matrices for use as affinity supports or for sample analysis. Similarly, antibodies or their binding fragments made or selected using the arginine analogs and/or conjugates of the present invention can also be immobilized on solid-phase matrices. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of *Immunoassay*, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001.

Surfaces such as those described above may be modified to provide linkage sites, for example by bromoacetylation, silation, addition of amino groups using nitric acid, and attachment of intermediary proteins, dendrimers and/or star polymers. This list is not meant to be limiting, and any method known to those of skill in the art may be employed.

3. Detectable Label Conjugates

Biological assays require methods for detection, and one of the most common methods for quantitation of results is to conjugate an enzyme, fluorophore or other detectable label to the molecule under study (e.g., using one or more arginine analogs of the invention), which may be immobilized for detection by a receptor molecule that has affinity for the molecule. Alternatively, the receptor to the molecule under study (e.g., an antibody or binding fragment thereof made or selected using the analogs or conjugates of the invention) may be conjugated to an enzyme, fluorophore or other detectable label. Enzyme conjugates are among the most common conjugates used. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g, biotin, digoxigenin, maltose, oligohistidine, 2,4-dintrobenzene, phenylarsenate, ssDNA, dsDNA, etc.).

Particularly preferred detectable labels are fluorescent latex particles such as those described in U.S. Pat. Nos. 5,763, 189, 6,238,931, and 6,251,687; and International Publication WO95/08772, each of which is hereby incorporated by reference in its entirety. Exemplary conjugation to such particles is described hereinafter.

Use of Arginine Analogs in Receptor Binding Assays

The arginine analogs and conjugates of the present invention may be advantageously used in receptor binding assays. Receptor binding assays include any assay in which a signal is dependent upon specific binding of an analyte to a cognate receptor, and include immunoassays, ligand-receptor assays, and nucleic acid hybridization assays.

The presence or amount of an analyte is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Numerous methods and devices are well known to the skilled artisan for the practice of receptor binding assays. See, e.g., U.S. Pat. Nos. 6,143,576; 6,113,855; 6,019,944; 5,985, 579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize detectably labeled molecules and antibody solid phases in various sandwich, competitive, or non-competitive assay formats, to generate a signal that is related to the presence or amount of an analyte of interest. One skilled in the art also recognizes that robotic instrumentation including but not limited to Beckman Access, Abbott AxSym, Roche ElecSys, Dade Behring Stratus systems are among the immunoassay analyzers that are capable of performing such immunoassays. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. As described herein, preferred assays utilize an antibody raised against an arginine analog conjugate (wherein the antibody is coupled to a solid phase or a detectable label), and/or an arginine analog conjugated to a detectable label, and/or an arginine analog conjugated to a solid phase.

In its simplest form, an assay device according to the invention may comprise a solid surface comprising receptor(s) that specifically bind one or more analytes of interest (e.g., dimethylarginine). For example, antibodies may be immobilized onto a variety of solid supports, such as magnetic or chromatographic matrix particles, the surface of an assay plate (such as microtiter wells), pieces of a solid substrate material or membrane (such as plastic, nylon, paper), and the like using the cross-linkers of the present invention. Such devices would preferably also contain one or more arginine analog conjugates that correspond to the one or more analytes of interest and that bind to the immobilized receptors. By "correspond to" it is meant that a particular arginine analog conjugate competes with an analyte of interest for binding to its receptor in the assay.

In similar fashion, an assay device may comprise a solid surface comprising one or more of the arginine analogs described herein immobilized thereon according to the methods of the present invention, where the one or more arginine analogs correspond to one or more analytes of interest. Such devices would preferably also contain one or more receptor(s) that specifically bind the analyte(s) of interest, where the receptors are conjugated to a detectable label.

Exemplary devices are described in Chapter 41, entitled "Near Patient Tests: Triage® Cardiac System," in *The Immunoassay Handbook*, $2^{nd}$ ed., David Wild, ed., Nature Publishing Group, 2001, which is hereby incorporated by reference in its entirety. In assay devices, flow of a sample along the flow path may be driven passively (e.g., by capillary, hydrostatic, or other forces that do not require further manipulation of the device once sample is applied), actively (e.g., by application of force generated via mechanical pumps, electroosmotic pumps, centrifugal force, increased air pressure, etc.), or by a combination of active and passive driving forces. Additional elements, such as filters to separate plasma or serum from blood, mixing chambers, etc., may be included as required by the artisan.

Preferred assay methods would comprise contacting a sample suspected of containing an analyte of interest with an arginine analog that corresponds to the analyte of interest, and with a receptor that specifically binds the analyte of interest, under conditions selected such that the arginine analog competes with an analyte of interest for binding to its receptor in the assay. In various embodiments, the arginine analog is conjugated to either a solid phase, or to a detectable label according to the methods described herein.

In the case where the arginine analog is conjugated to a solid phase, the receptor is preferably conjugated to a detectable label. A signal is generated from the receptor-label conjugate that binds to the arginine analog coupled to the solid phase. Because of the competition between the analyte and the arginine analog-solid phase conjugate for binding to the labeled receptor, the signal generated is inversely related to the amount of analyte present in the sample.

In the case where the arginine analog is conjugated to a detectable label, the receptor is preferably conjugated to a solid phase. A signal is generated from the arginine analog-label conjugate that binds to the receptor coupled to the solid phase. Because of the competition between the analyte and the arginine analog-label conjugate for binding to the receptor coupled to the solid phase, the signal generated is inversely related to the amount of analyte present in the sample.

The analysis of a plurality of analytes may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) inununoassay system, etc. Preferred apparatuses or protein chips perform simultaneous assays of a plurality of analytes on a single surface. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

EXAMPLES

The following examples serve to illustrate the present invention. These examples are in no way intended to limit the scope of the invention.

Example 1

Synthesis of Amino-Substituted Thioester Derivative of ADMA

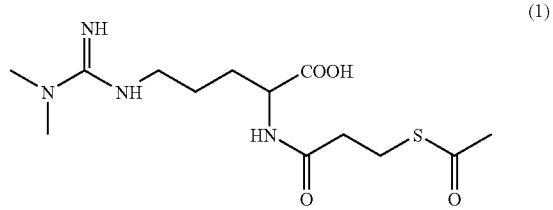

ADMA (47.99 g, Sigma-Aldrich) was added to a 10 mL round-bottom flask. Acetonitrile (1 mL) was added, followed by solid N-succinimidyl-S-acetylthiopropionate (SATP, 73 mg, Molecular Bioscience, Inc.), and the mixture stirred until dissolved. Dry diisopropylethylamine (86 μL) was added, and the flask purged with argon and sealed. The reaction mixture was sonicated, and stirred overnight at room temperature.

The solid product (1) was collected by filtration, rinsed with 2×1 mL acetonitrilen and 2×1 mL ethyl ether.

Example 2

Synthesis of N-bromoacetyl-L-homocysteine Thiolactone (2)

Pyridine (1.7 mL) was added to a stirring solution of bromoacetic acid and L-homocysteine thiolactone hydrochloride (1.54 g) in dry dimethylformamide (50 mL). The solution was treated with 1-Ethyl-3-(3-dimethylaminopropyl)-carbodiimide (2.11 g), and stirred overnight at room temperature under an argon atmosphere. The dimethylformamide was evaporated, and the residue treated with 20 mL water. The product (2) was collected by filtration, washed with water a second time, and dried under vacuum.

Example 3

Synthesis of Amino-Substituted Thiolactone Derivative of ADMA

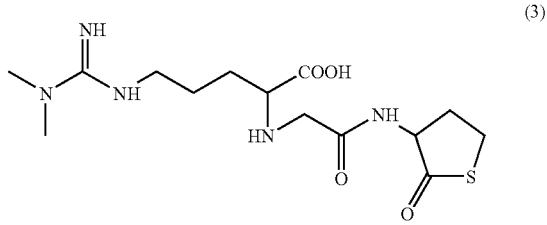

(3)

ADMA (50 mg) and (2) (64 mg) were stirred in dimethylformamide (2.5 mL), and diisopropylethylamine (130 μL was added. The reaction mixture was stirred at 80° C. under argon for 5 days. The dimethylformamide was evaporated under vacuum, and the residue dissolved in water (3 mL), which was then extracted with methylene chloride (3×5 mL), which was centrifuged to effect complete phase separation. The clear aqueous layer was collected, evaporated, and the residue treated with methylene chloride and re-evaportaed and dried under vacuum. The solid material was triturated with methylene chloride (2×5 mL) and dried. The solids were then treated with 2 mL ethanol, sonicated, and triturated with 2 mL ethanol, followed by drying to afford (3).

Example 3

Synthesis of Carboxyl-Substituted Thiolactone Derivative of ADMA

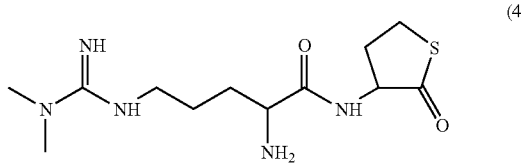

(4)

A solution of t-boc-$N^G,N^G$-dimethylarginine-L-homocysteine thiolactone (22 mg) in methylene chloride (500 μL) was treated with trifluoroacetic acid (500 μL), and allowed to stand at room temperature for 2 hours. The solvent was evaporated, and the clear residue dried under vacuum. The residue was then treated with ether (1 mL), sonicated, and evaporated to remove residual trifluoroacetic acid. The residue was again treated with ether (1 mL), and precipitated as a solid. The solid was triturated with ether (1 mL) and dried under vacuum to afford (4).

Example 4

Synthesis of KLH-SMCC

Keyhole Limpet Hemocyanin (KLH, Calbiochem #374817, 50 mg/mL in glycerol) was passed through a 40 mL GH25 column equilibrated in in 0.1M potassium phosphate, 0.1M borate, 0.15M sodium chloride buffer, pH 7.5 to remove glycerol. A 1.5-fold molar excess of N-ethylmaleimide was added, and the mixture incubated 30 minutes at room temperature. A 200-fold molar excess of sulfo-SMCC (Pierce #22322) from a 50 mM stock in distilled water was added while vortexing. Vortexing was continued for another 30 seconds, followed by incubation for 10 minutes at room temperature. A 100-fold molar excess of SMCC (Pierce #22360) from an 80 mM stock in acetonitrile was added while vortexing. 1M KOH was added to maintain a pH of between 7.2 and 7.4. The mixture was stirred at room temperature for 90 minutes. After 90 minutes incubation, KLH-SMCC was purified by gel filtration using a GH25 column equilibrated in 0.1M potassium phosphate, 0.02M borate, 0.15M sodium chloride buffer, pH 7.0.

Example 5

Arginine Analog Conjugates

Compounds (1), (3) and (4) were conjugated to KLH-SMCC as follows. Derivatives were incubated as 20 mM stock solutions in KOH (0.25×vol of 1N) to hydrolyze the protective group to provide free thiol, followed by neutralization to pH 7.0. a 2-fold molar excess (based on the concentration of SMCC in a particular batch of KLH-SMCC) of derivative was added to KLH-SMCC, and the mixture stirred for 2 hours at room temperature. Conjugates were collected by gel filtration.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound or salt thereof, said compound having the structure:

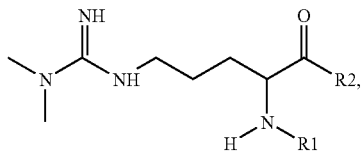

wherein:
R$^1$ is —H or a conjugating group having the structure

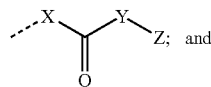

R$^2$ is —OH or a conjugating group having the structure

X is an optionally present C$_{1-4}$ unsubstituted alkylene;
Y is an optionally substituted C$_{1-4}$ alkylene or N(H)—C$_{1-6}$ alkylene, and is optionally present; and
Z is a 5- or 6-member cyclic thiolactone, an optionally substituted C$_{1-4}$ thiol-substituted alkyl, or an optionally substituted thioester having the structure

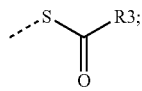

R$^3$ is selected from the group consisting of optionally substituted C$_{1-4}$ alkyl, optionally substituted C$_{1-4}$ alkoxy, and optionally substituted aryl;
said substitution(s), when present, are independently selected from the group consisting of C$_{1-6}$ alkyl straight or branched chain, benzyl, halogen, trihalomethyl, C$_{1-6}$ alkoxy, —NO$_2$, —NH$_2$, —OH, =O, —COOR' where R' is H or lower alkyl, —CH$_2$OH, and —CONH$_2$; and
one but not both of R$^1$ or R$^2$ is a conjugating group.

2. A compound or salt thereof according to claim 1, wherein R$^1$ is H, and R$^2$ is a conjugating group having the structure

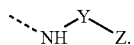

3. A compound or salt thereof according to claim 2, wherein Y is absent and Z is a thiolactone.

4. A compound or salt thereof according to claim 3, wherein said thiolactone has 5 ring members.

5. A compound or salt thereof according to claim 2, wherein Y is N(H)—C$_{0-6}$ alkyl and Z is a thioester.

6. A compound or salt thereof according to claim 5, wherein Y has the structure
—N(H)CH$_2$C(O)CH$_2$—.

7. A compound or salt thereof according to claim 6, wherein R$^3$ is selected from the group consisting of —CH$_3$, —CH$_2$CH$_3$, —OCH$_3$, —OCH$_2$CH$_3$, —OCH$_2$C$_6$H$_5$, —OCH$_2$CH$_2$C$_6$H$_5$, and —C$_6$H$_5$.

8. A compound or salt thereof according to claim 2, wherein R$^1$ is H, and R$^2$ is a conjugating group having the structure:

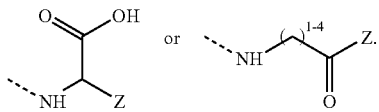

9. The compound or salt thereof according to claim 8, wherein Z is an alkyl thiol.

10. The compound or salt thereof according to claim 9, wherein Z is —(CH$_2$)$_{1-2}$SH.

11. The compound or salt thereof according to claim 1, wherein R$^2$ is —OH, and R$^1$ is a conjugating group having the structure

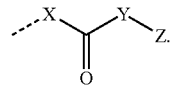

12. The compound or salt thereof according to claim 11, wherein X is C$_{0-4}$ unsubstituted alkylene, Y is N(H), and Z is a thiolactone.

13. The compound or salt thereof according to claim 12, wherein Z has 5 ring members.

14. The compound or salt thereof according to claim 11, wherein Y is C$_{0-4}$ alkylene and Z is a thioester.

15. The compound or salt thereof according to claim 14, wherein X is absent.

16. The compound or salt thereof according to claim 15, wherein R$^3$ is selected from the group consisting of —CH$_3$, —CH$_2$CH$_3$, —OCH$_3$, —OCH$_2$CH$_3$, —OCH$_2$C$_6$H$_5$, —OCH$_2$CH$_2$C$_6$H$_5$, and —C$_6$H$_5$.

17. The compound or salt thereof according to claim 11, wherein X is C$_{0-4}$ unsubstituted alkylene, Y is N(H) or absent, and Z is a C$_{1-4}$ thiol-substituted alkyl.

18. The compound or salt thereof according to claim 17, wherein Z has the structure:

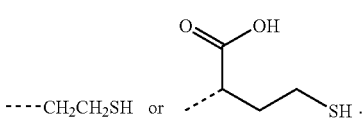

19. A compound selected from the group consisting of:

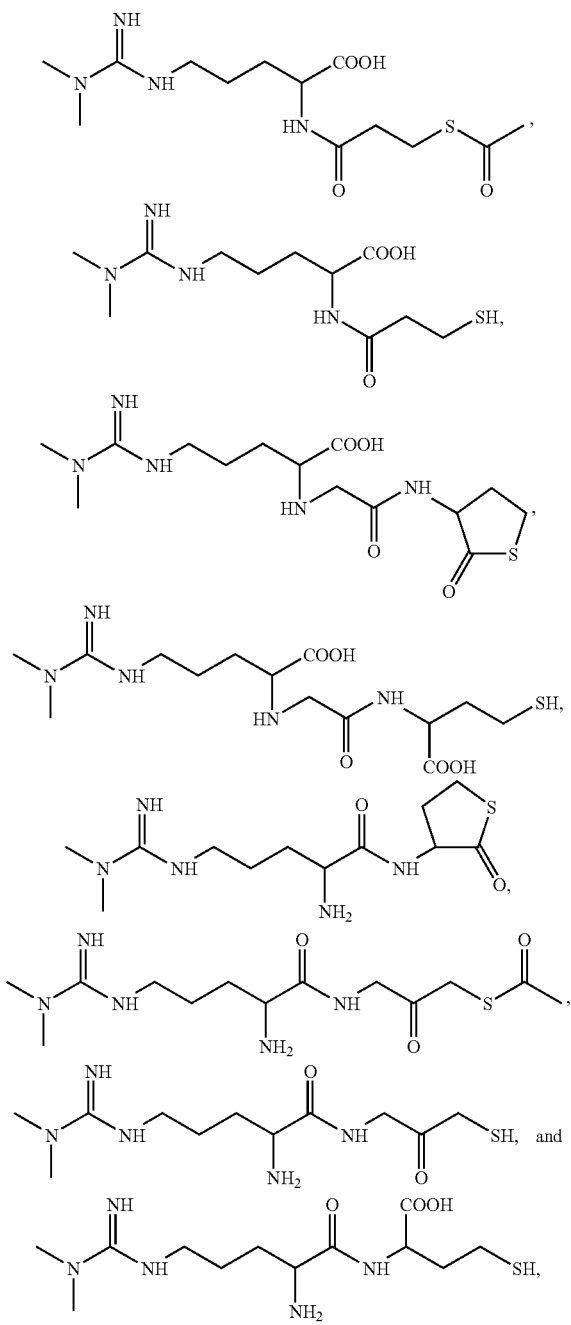

or a salt thereof.

20. A conjugate comprising a compound according to claim 1 covalently bound through a sulfhydryl group on the compound(s) to a sulfhydryl-reactive moiety on a protein, polypeptide, detectable label, nucleic acid, or solid phase.

21. The conjugate according to claim 20, wherein said sulfhydryl-reactive moiety is selected from the group consisting of a maleimide, an alkyl halide, an aryl halide, an alpha-haloacyl, and a pyridyl disulfide.

22. The conjugate according to claim 21, wherein said sulfhydryl-reactive moiety is a maleimide, whereby said compound(s) are covalently bound to said protein, polypeptide, detectable label, nucleic acid, or solid phase to provide one of the following structures:

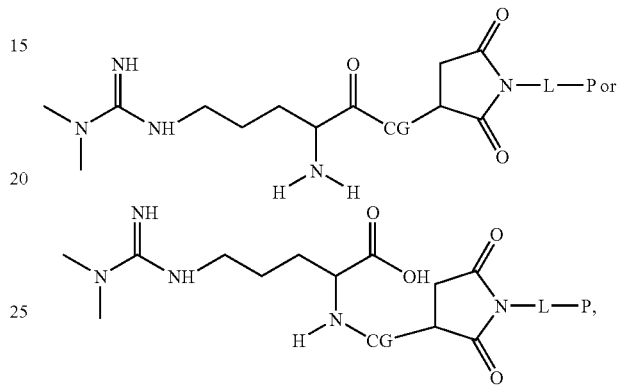

wherein:
CG is a conjugating group covalently bound to the maleimide moiety through a thiol linkage,
L is a covalent bond, or a linker comprising 1-10 backbone atoms, of which 0-4 backbone atoms are heteroatoms, wherein L is optionally substituted with from 1 to 4 substituents independently selected from the group consisting of $C_{1-6}$ alkyl straight or branched chain, —$NO_2$, —$NH_2$, =O, halogen, trihalomethyl, $C_{1-6}$ alkoxy, —OH, —$CH_2OH$, and —C(O)$NH_2$, and
P is said protein, polypeptide, detectable label, nucleic acid, or solid phase.

23. The conjugate according to claim 21, wherein said detectable label is selected from the group consisting of an enzyme, a fluorophore, biotin, avidin, streptavidin, digoxigenin, maltose, oligohistidine, 2,4-dintrobenzene, phenylarsenate, and a fluorescent latex particle.

24. The conjugate according to claim 21, wherein said protein is keyhole limpet hemocyanin or bovine serum albumin.

25. The conjugate according to claim 21, wherein said compound(s) are bound to a solid phase selected from the group consisting of a membrane, a cellulose-based paper, a polymeric particle, a latex particle, a paramagnetic particle, a glass substrate, a silicon substrate, a plastic substrate, and a multiple-well plate.

* * * * *